(12) United States Patent
Landers

(10) Patent No.: US 6,908,643 B2
(45) Date of Patent: Jun. 21, 2005

(54) METHOD AND COMPOSITION FOR DETERRING ANIMALS FROM CHEWING ON WOOD

(76) Inventor: Phillip G. Landers, 5312 Vista Club Run, Sanford, FL (US) 32771

( * ) Notice: Subject to any disclaimer, the term of this patent is extended or adjusted under 35 U.S.C. 154(b) by 14 days.

(21) Appl. No.: 10/364,814

(22) Filed: Feb. 11, 2003

(65) Prior Publication Data

US 2003/0152710 A1 Aug. 14, 2003

Related U.S. Application Data

(60) Provisional application No. 60/356,275, filed on Feb. 12, 2002.

(51) Int. Cl.[7] .................................................. B05D 3/00
(52) U.S. Cl. ..................................................... 427/385.5
(58) Field of Search ................................ 427/384, 385.5

(56) References Cited

U.S. PATENT DOCUMENTS 6,237,305 B1 * 5/2001 Landers ................... 52/741.14
6,576,673 B2 * 6/2003 Landers ....................... 514/675

FOREIGN PATENT DOCUMENTS

FR        2222013        * 10/1974

* cited by examiner

*Primary Examiner*—Erma Cameron
(74) *Attorney, Agent, or Firm*—William M. Hobby, III

(57) ABSTRACT

A method and composition of material for coating the surface of a structure to prevent animals from chewing on the structure. The composition includes Isophorone, organo-clay absorber, Bisphenol A Diglycidal Ether Polymer and a polyamide resin hardener. It may also have glass flakes or mica therein as well as a microencapsulated acrylic resin-based sealant and a flocculated silica thickener. The method includes preparing the composition having the Isophorone in a polymer resin, mixing the polymer hardener to the prepared composition to form a coating composition, and coating the surface, such as a piece of wood, with the coating composition to prevent animals from chewing on it. Coating may be by painting or troweling the composition onto the structure.

8 Claims, No Drawings

METHOD AND COMPOSITION FOR DETERRING ANIMALS FROM CHEWING ON WOOD

This application claims the benefit of Provisional Application No. 60/356,275, filed Feb. 12, 2002.

BACKGROUND OF THE INVENTION

Wood, often treated with toxic wood preserving chemicals, is used in the construction of fences, stalls, corrals, and other structures to contain and house domestic and exotic animals and birds. These toxic chemical preservatives include, but are not limited to, creosote, pentachlorophenol, and arsenic salts, such as copper chromated arsenic. Chewing on and ingestion of both treated and untreated wood is known to cause severe medical problems and even the death of these animals. In addition, wood chewing can compromise the structural integrity and aesthetic appeal of the wood. Examples of such chewing can be found in domestic animals, such as dogs that chew on woodwork and furniture and horses that chew and "crib" on wooden fences, stalls, posts, and other wood structures used to house and contain them. Wood chewing by more exotic zoo animals is also prevalent.

While possibly not the worst of the wood chewing animals, horses, because of their numbers, inflict significant economic damage as a result of cribbing and wood chewing. It is thought that when a horse cribs on wood, his body releases endorphins, natural "drugs" which stimulate the pleasure center of his brain, so that he receives a "reward" ("pleasure drug") every time he cribs. Often cribbers would rather crib than eat. Wood chewing horses can suffer colic from eating wood splinters.

This invention describes a compound that can be painted on wood structures to deter animals from chewing and cribbing.

Isophorone (3,5,5-trimethyl-2-cyclohen-one-1) compounds have been shown effective in deterring woodpeckers when painted on wood. Isophorone compounds have been shown in my U.S. Pat. No. 6,237,305 to be highly effective in penetrating and sealing wood. While effective on woodpeckers, field tests have shown that these formulations, while effective for woodpecker deterrence, do not provide long-term protection against wood chewing by larger animals, such as horses. The present invention describes a chewing deterring coating that encapsulates and time-releases an odor that most animals find offensive. This invention is an improvement over my previously patented isophorone deterrent technology as it identifies the sense being affected and extends the effectiveness from woodpeckers to other animals, such as horses and dogs.

The invention involves the use of isophorone, absorbed in a highly absorbent organo-clay, barriered by glass flake or mica, and encased in a chemically-resistant epoxy or other polymer matrix. The highly absorbent organo-clay is used to trap the isophorone. The glass flake or mica controls the dissipation of the volatile solvent by forming a mechanical structure of overlapping glass platelets. The chemical resistant polymer matrix binds and adheres the composition to the surface. Capsules of micro-encapsulated isophorone sealant, described in my patent application "Method of Deterring Woodpeckers", may also be incorporated to reinforce the deterrence to increase the odorant level in the coating. While the deterring odor is constantly being released, the odor gets worse when the coating surface is breached. This reinforces the "behavior" training and preventing the animal from further chewing.

The above described coating is applied to exposed wood or other surfaces as a chewing deterrent to animals, such as horses, dogs, cats, squirrels, and other larger animals.

SUMMARY OF THE INVENTION

A method and composition of material for coating the surface of a structure to prevent animals from chewing on the structure. The composition includes Isophorone, organo-clay absorber, Bisphenol A Diglycidal Ether Polymer and a polyamide resin hardener. It may also have glass flakes or mica therein as well as a microencapsulated acrylic resin-based sealant and a flocculated silica thickener. The method includes preparing the composition having the Isophorone in a polymer resin, mixing the polymer hardener to the prepared composition to form a coating composition, and coating the surface, such as a piece of wood, with the coating composition to prevent animals from chewing on it. Coating may be by painting or troweling the composition onto the structure.

DESCRIPTION OF THE PREFERRED EMBODIMENT

The present invention describes a method of deterring animals, and especially larger animals, such as horses, from chewing on structures and utilizing a coating that generates a deterrent smell when released by the animal chewing thereon. Isophorone is absorbed in a highly absorbent organo-clay, mixed with glass flake or mica, and blended into a chemically resistant structural polymer matrix. It will be clear that other methods of entrapping the isophorne may also be utilized. When applied as a paint, a layer of overlapping glass platelets is formed that controls dissipation of the isophorone that is absorbed in an organo clay forming chemically resistant structural matrix. Concentration of the isophorone sealant compound can be increased by the addition of isophorone encapsulated pellets. Different sized pellets can be used to enhance the results.

A preferred resin composition by weight includes 8–15% Glass Flake or mica; 5–10% organo-clay absorber; 40–50% Isophorone (3,5,5-trimethyl-2-cyclohexen-one-1); 25–35% Bisphenol A Diglycidal Ether Polymer; 1–2% of a flocculated silica thickener; 1–2% of various color pigments; and optionally 8–20% micro-encapsulated acrylic resin-based sealant (optional). The preferred hardener composition is 10–20% polyamide resin.

EXAMPLE

A specific formula includes by weight 9% Glass Flake or mica; 6% organo-clay absorber; 37% Isophorone (3,5,5-trimethyl-2-cyclohexen-one-1); 26% Bisphenol A Diglycidal Ether Polymer; 1% of a flocculated silica thickener; and 1% of various color pigments. A preferred hardener composition is 20% polyamide resin.

The preferred volatile liquid is Isophorone (3,5,5-trimethyl-2-cyclohexen-one-1) obtained from Union Carbide. The glass flake is 1/32" Glass Flake obtained from Glass Flake International but mica can also be used. The clay thickener is Claytone APA from Southern Clay Products and the flocculated silica thickener is Degusa Aerosil 200. The polymer resin is Bisphenol A Diglycidal Ether obtained from Shell Chemical under their formulation Epon 828. The polyamide resin is obtained from Cognis Corporation under their formula Versamid 140.

The composition as set forth in the example can be applied to a wooden fence top rail or the top rail of a corral, for instance holding horses, which are well known to chew on rails of an enclosure. The composition is applied by painting, flow coating, or troweling the top of the wood railings which is the portion primarily chewed on by the horses. However, other sections can be coated as needed. A coating has the advantage of laying out the glass or mica flakes in a flat horizonal layer since a coating does not leave room for the glass to remain edgewise. The isophorone odor is slowly released at levels that are barely perceptible by humans (approximate 0.2 ppm) but are well within the range perceptible by various animals, such as horses and dogs. An animal chewing through the material and the glass will pass through the layer of overlapping glass platelets or other material that traps the isophorone released. The isophorone can be encapsulated into different size pellets as desired which pellets are broken upon an animal biting into the coating.

The method includes the mixing of an isophorone formula in accordance with the above example, applying the coating to a chewing surface, such as a wooden rail or the like, and then painting or troweling the coating on in a thin coat evenly and allowing the coating to cure. The coating can be applied to posts around stalls, especially in feeding areas; onto live trees or onto a paper wrapping around a live tree; to fence rails, starting with the top rail and then to the lower rails; and to telephone poles. However, the present invention should not be construed as limited to the forms disclosed which should be considered illustrative rather than restrictive.

I claim:

1. A method of coating a surface to prevent animals from chewing on the surface including the steps of:

preparing a composition comprising isophorone, an organic-clay absorber, glass or mica flakes, and a polymer resin;

mixing a polymer hardener to the prepared composition to form a coating composition; and coating the surface of a structure with said coating composition to prevent animals from chewing on the structure.

2. The method of coating a surface to prevent animals from chewing on the surface in accordance with claim 1 in which the step of coating the surface of a structure includes troweling said coating composition onto the surface.

3. The method of coating a surface to prevent animals from chewing on the structure in accordance with claim 1 in which the step of preparing a composition includes a composition having flocculated thickener therein.

4. The method of coating a surface to prevent animals from chewing on the structure in accordance with claim 1 in which the step of preparing a composition includes a composition having micro-encapsulated acrylic resin therein.

5. The method of coating a surface to prevent animals from chewing on the structure in accordance with claim 4 in which the step of preparing a composition includes preparing a composition with 30–50 percent by weight of isophorone.

6. The method of coating a surface to prevent animals from chewing on the structure in accordance with claim 5 in which the step of preparing a composition includes preparing a composition with 25–35 percent by weight of bisphenol A diglycidal ether polymer.

7. The method of coating a surface to prevent animals from chewing on the structure in accordance with claim 1 in which the step of preparing a composition includes preparing a composition with 5–10 percent by weight of glass flakes.

8. The method of coating a surface to prevent animals from chewing on the structure in accordance with claim 1 in claim which the step of mixing a polymer hardener includes mixing 10–20 percent by weight of a polyamine resin.

* * * * *